(12) United States Patent
Hanna

(10) Patent No.: US 6,596,006 B1
(45) Date of Patent: Jul. 22, 2003

(54) SURGICAL INSTRUMENT OF LAMELLAR CUTTING OF THE CORNEA

(75) Inventor: Khalil Hanna, Paris (FR)

(73) Assignee: HumanOptics AG, Erlangen (DE)

(*) Notice: Subject to any disclaimer, the term of this patent is extended or adjusted under 35 U.S.C. 154(b) by 0 days.

(21) Appl. No.: 09/889,676

(22) PCT Filed: Feb. 7, 2000

(86) PCT No.: PCT/FR00/00276

§ 371 (c)(1),
(2), (4) Date: Jul. 19, 2001

(87) PCT Pub. No.: WO00/47146

PCT Pub. Date: Aug. 17, 2000

(51) Int. Cl.$^7$ .................................................. A61F 5/00
(52) U.S. Cl. ....................................................... 606/166
(58) Field of Search ................................ 606/166, 167, 606/180, 169, 171–173, 176–178; 604/19, 22

(56) References Cited

U.S. PATENT DOCUMENTS 4,173,980 A    11/1979    Curtin ......................... 128/303

FOREIGN PATENT DOCUMENTS

| WO | 9406356 | 3/1994 |
| WO | 9531143 | 11/1995 |
| WO | 9810716 | 3/1998 |
| WO | 9818517 | 5/1998 |
| WO | 9827901 | 7/1998 |
| WO | 9903433 | 1/1999 |
| WO | 0895765 | 2/1999 |

Primary Examiner—Kevin T. Truong
Assistant Examiner—Victor Nguyen
(74) Attorney, Agent, or Firm—Birch, Stewart, Kolasch & Birch, LLP

(57) ABSTRACT

A surgical instrument for lamellal cutting of the cornea, the instrument comprising:
  a ring-shaped base (1) shaped for being applied to and held against the eye; and
  a cutting tool having a cutting blade received in a support (4) co-operating with the base (1) to guide displacement of the cutting edge of the blade in a plane parallel to the ring, and including, in front of the blade, a shaping element (10) for shaping the portion of the cornea that projects into the ring;
wherein the shaping element is constituted by a roller (10) coupled to the blade support about an axis of rotation perpendicular to the cutting direction.

21 Claims, 1 Drawing Sheet

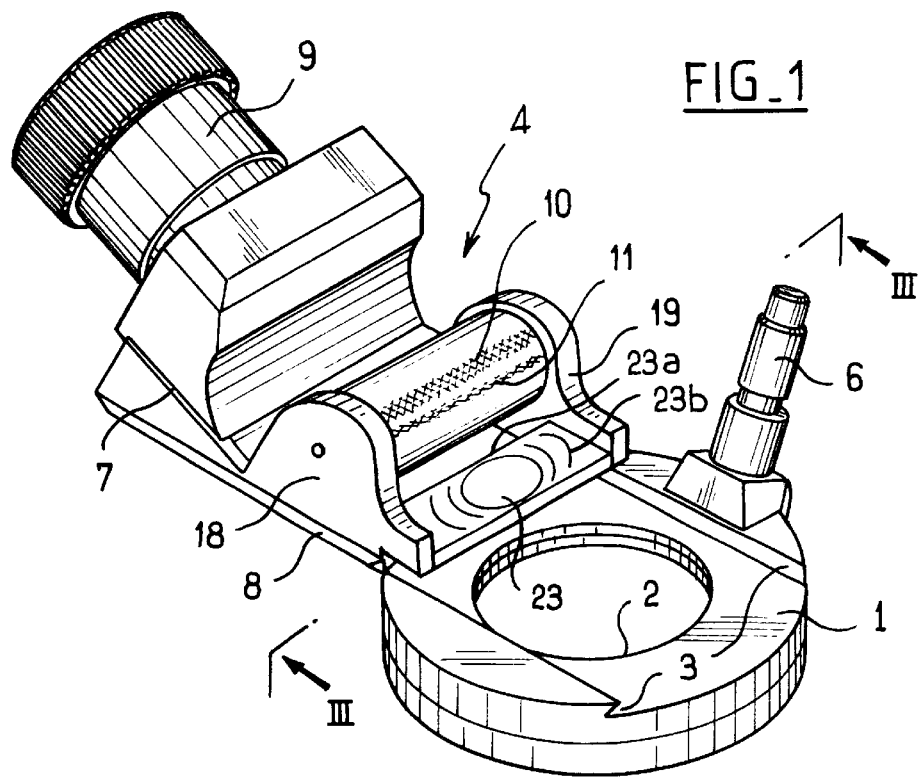
FIG_1
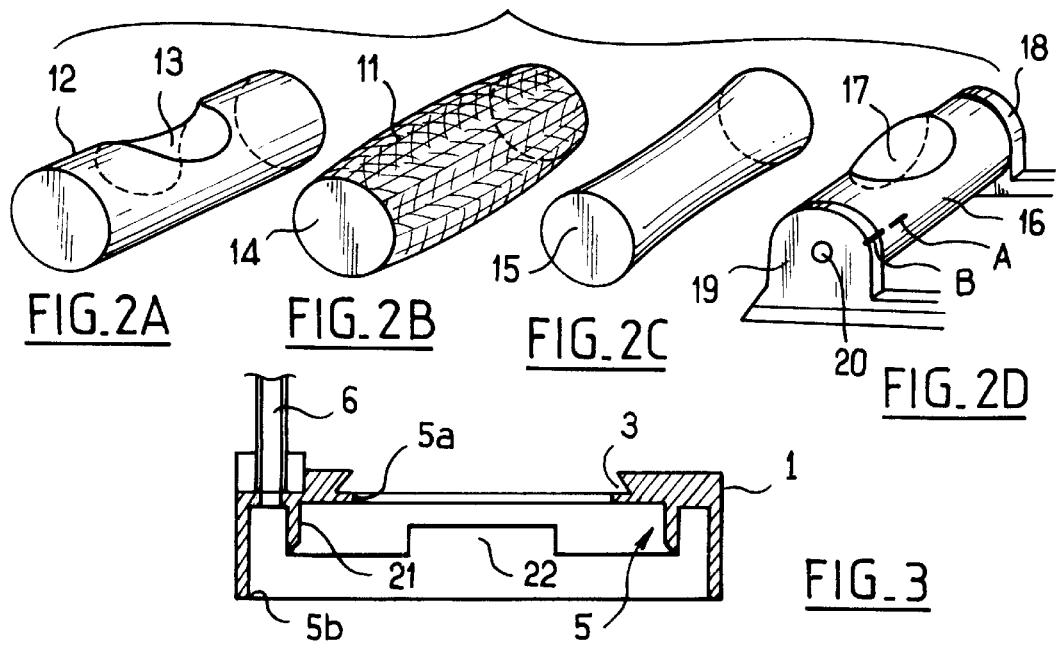
FIG_2
FIG_2A  FIG_2B  FIG_2C  FIG_2D
FIG_3

SURGICAL INSTRUMENT OF LAMELLAR CUTTING OF THE CORNEA

This application is the national phase under 35 U.S.C. §371 of PCT International Application No. PCT/FR00/00276 which has an International filing date of Feb. 7, 2000, which designated the United States of America and was not published in English.

BACKGROUND OF THE INVENTION

Surgery to correct ametropia using the technique of Prof. Barraquer in combination with an excimer laser is a surgical technique that is now widely developed and used on a large scale. It makes use of surgical instruments known as "microkeratomes" which essentially comprise a ring for fixing on the eye to be operated on so that the cornea projects into the center of the ring, and a moving cutting device guided relative to the fixing ring and comprising firstly a surface for flattening of the portion of the cornea that projects into the ring and secondly a generally-oscillating cutting blade whose cutting edge is situated immediately behind the flattening surface and at a determined distance therefrom measured vertically so as to define the thickness of the corneal lamella which is thus subjected to resection.

SUMMARY OF THE INVENTION

The present invention is a variant embodiment of known instruments for cutting the cornea as used in the Barraquer technique.

To this end, the invention provides a surgical instrument for performing lamellar cutting of the cornea and comprising:

- a ring-shaped base shaped for being applied to and held against the eye; and
- a cutting tool having a cutting blade received in a support co-operating with the base to guide displacement of the cutting edge of the blade in a plane parallel to the ring, and including, in front of the blade, a shaping element for shaping the portion of the cornea that projects into the ring, wherein the shaping element is constituted by a roller coupled to the blade support about an axis of rotation perpendicular to the cutting direction.

Thus, unlike existing instruments, the cornea is no longer shaped by a plate which compresses it, but by a member which rolls on the cornea without sliding, thus making it possible firstly to obtain resection of thickness that is uniform or non-uniform in the transverse direction, and secondly to vary the thickness of the resection as cutting advances. Thus a flattening plate makes it possible to perform resection that is parallel only to the anterior surface of the cornea, whereas the roller of the invention makes it possible to perform resection of varying profile, and in particular of profile that is parallel to the posterior surface of the cornea which is known to be thicker at the periphery than in the center. This makes it possible in a single resection operation to modify the curvature of the cornea in order to correct ametropia, once it has been determined what shape needs to be given to the outside surface of the cornea, and thus what profile it is to have after correction. It is also possible with the instrument of the invention to combine mechanical resection of a corneal flap of determined profile and then to add additional resection of a lenticule or some other portion of the stroma before folding down the flap.

Thus, in the instrument of the invention, the roller can be either cylindrical, or barrel-shaped, or diabolo-shaped. It can also be given any other useful shape, and in particular it can be cylindrical and possess a lens applied in relief on its outside surface. In the same manner, it can be cylindrical and possesses a lens-shaped depression in its outside surface. When its outside surface is not a surface of revolution, the roller should have an index associated with the position of a particular generator line on its peripheral surface and the support should include a mark for locating the index in a determined position, in particular at the beginning of an operation.

Advantageously, the peripheral surface of the shaper member is provided with microrelief to enhance rolling without slip on the surface of the cornea.

Furthermore, and in particular for large-diameter cuts, it can be advantageous to place a plate in front of the roller so as to avoid pressure variations in the eye. The distance between the blade and the rear edge of the plate can be about 5 millimeters (mm) to 6 mm.

Finally, and also advantageously, the annular base has a groove in its face directed towards the eye, the groove being partitioned by an intermediate wall provided with at least one opening providing communication between the two portions of the groove.

BRIEF DESCRIPTION OF THE DRAWINGS

Other characteristics and advantages of the invention appear from the following description of embodiments of the invention given below as non-limiting examples.

Reference is made to the accompanying drawing, in which:

FIG. 1 is a diagrammatic view of means forming the instrument of the invention;

FIG. 2 shows four possible variant embodiments of a cornea-shaping roller; and

FIG. 3 is a section view through the eye-holding ring forming part of the instrument of the invention.

MORE DETAILED DESCRIPTION

FIG. 1 shows a ring 1 for fixing to an eye which is to be operated on, the ring being conventional in itself and possessing a central opening 2 through which the cornea projects. The ring is provided with a guide 3, in this case in the form of a dovetail groove by way of example, suitable for slidably receiving a carriage 4 constituting a carrier for a blade for cutting the cornea. The face of the ring 1 in contact with the eye (FIG. 3) defines a space 5 limited by the bottom edge 5b of a lateral skirt and by the bottom edge 5a of the opening 2, such that when these two edges 5a and 5b are in contact with the conjunctiva of the eye, defines a chamber that can be partially evacuated by means of a duct 6. The ring 1 is thus fixed to the eye by suction.

The blade-carrying carriage 4 shown in FIG. 1 has no limiting character concerning the means of the invention. Thus, the invention applies to any keratoma whether manual or automatic, i.e. motor-driven, providing it has a blade-carrying carriage capable of being moved in a plane parallel to the plane of the ring 1 along a path that is rectilinear or curved, thus making it possible to cut off a corneal disk or to cut open a corneal flap.

The carriage 4 shown includes a housing 7 which receives in conventional manner a blade capable of oscillating transversely to the dovetail guide 8 at the bottom of the carriage for co-operating with the dovetail groove 3 in the ring. An element 9 belonging to the carriage 4 represents drive means for the blade and/or drive means for moving the carriage 4 relative to the ring 1.

In front of the edge of the blade situated at the bottom of the housing 7, the carriage 4 carries a cornea-shaping member between the guides 8, which member is formed by a roller 10. The roller is positioned precisely above the edge of the blade so that the portion of the cornea deformed by the roller is of controlled thickness, thereby constituting a criterion that determines the cut made. The roller 10 is designed to roll on the cornea without slip and for this purpose it includes microrelief 11 on its outside surface.

FIG. 2 shows various embodiments of the roller 10 for obtaining particular profiles of cut. Portion 2A of FIG. 2 shows a cylindrical roller 12 from which a surface lenticule has been removed so that the roller possesses a depression 13. Portion 2B of the Figure shows a roller 14 that is barrel-shaped. Portion 2C shows a roller 15 which is diabolo-shaped, and portion 2D of FIG. 2 shows a roller 16 which is cylindrical and has a lens-shaped projection 17 on its peripheral surface. The projection 17 can be applied by any fixing means, and in particular by adhesive. The lens 17 is of a diameter that is appropriate for the operation. For example, in order to perform resection parallel to the posterior face of the cornea, a lens is used with a fine edge and thickness in the center that is one- to two-tenths of a millimeter thicker than the edge, depending on the selected diameter.

The rotary support for each of the rollers 10 to 16 is constituted by two arms 18, 19 standing on the "forearms" of the carriage 4 and suitable for having rollers snap-fastened between them and held securely. For example, the arms 18 and 19 can receive a shaft 20 which is mounted so that it does not rotate relative to the arms 18 and 19, and the rollers can be formed with a tubular member having a ball-bearing mount on the fixed shaft 20. Friction should be minimized as much as possible between the roller and the blade-carrying carriage 4 so as to enable the roller to roll without slip on the surface of the cornea.

The shaft 20 of the cylindrical cornea shaper of the invention extends parallel to the cutting edge of the blade, i.e. perpendicular to the guide 8. In other words, this shaft extends transversely relative to the advance movement of the carriage 4 as cutting of the cornea progresses.

Finally, it can be seen in portion 2D of FIG. 2 that an index A is present on the roller 16 suitable for being aligned with a mark B carried on one of the arms 18, 19 of the carriage 4, with the state of the instrument when the index is in register with the mark corresponding to beginning an operation, for example. It will be understood that such an index and mark are not necessary if the outer surface of the roller is a surface of revolution about the shaft 20. However they are necessary when the profile of cut to be obtained is special and requires a shaping roller to be used whose outside surface is not a surface of revolution about the axis of rotation of the roller.

In FIG. 1, there can be seen a fixed plate in front of the roller 10 between the arms 18 and 19, where the function of the plate is to pre-compress the cornea so as to avoid pressure variations in the eye having effects on how the eye is cut. This plate is useful in particular when making cuts of large diameter. In preferred manner, the distance between the rear edge 23a of the plate and the cutting blade is 5 mm to 6 mm. In addition, the plate 23 is advantageously transparent and carries graduations 23b for inspecting the dimensions of the flattened portion of the cornea.

FIG. 3 is a diametral section of the ring 1 on plane III—III of FIG. 1. The section of this ring 1 is itself known, except for the partition 21 which extends between the edges 5a and 5b of the groove 5 and which forms the suction chamber when the ring is in place on the eye, this partition being intended to rest likewise on the outside surface of the eye (the conjunctiva) and has the function of ensuring that in the event of conjunctiva becoming unstuck or torn away, it does not plug the outlet of the pipe 6 into the groove 5. In order to allow the two portions of the groove 5 as partitioned in this way to communicate with each other, the intermediate wall 21 includes notches 22 for ensuring permanent communication between the two portions.

What is claimed is:

1. A surgical instrument for cutting a lamellar flap of an eye cornea comprising:

a ring-shaped base having means for fixation to the eye;

a cutting tool having a support for a cutting blade with a cutting edge, said cutting blade oscillating in said support along a direction of said cutting edge, said support being provided with a corneal shaping element located in front of said cutting edge for engaging a portion of the cornea that projects into said ring-shaped base; and first and second guides provided on said base and said support, said guides guiding movement of said support across said base, wherein said shaping element is constituted by a roller coupled to said support, said roller having an axis of rotation which is at least substantially parallel to said cutting edge or perpendicular to a movement direction of said support across said base.

2. An instrument according to claim 1, wherein said roller is one of cylindrical-shaped, barrel-shaped, and diabolo-shaped.

3. An instrument according to claim 1, wherein said roller is cylindrical and possesses a lens fitted to project from its outer surface.

4. An instrument according to claim 1, wherein said roller is cylindrical and possesses a lens-shaped recess in its outer surface.

5. An instrument according to claim 1, wherein said roller includes an index associated with the position of its peripheral surface, and wherein said support includes a mark for locating the index in a determined position.

6. An instrument according to claim 1, wherein a peripheral surface of said roller is provided with microrelief to enhance rolling without slip on the surface of the cornea.

7. An instrument according to claim 1, including a cornea-pre-compressing plate in front of said roller.

8. An instrument according to claim 7, wherein said plate is transparent and includes graduations forming a template for inspecting the cornea.

9. An instrument according to claim 1, wherein said base has a face for engaging the eye, said face having a groove partitioned in two annular portions by an intermediate wall provided with at least one opening providing communication between said two portions of said groove.

10. A microkeratome for cutting a thin flap of tissue from a cornea of a patient's eye, the microkeratome comprising:

a base shaped for being applied to and held against the eye;

a first guide provided on said base;

a carriage including a second guide to cooperate with said first guide, such that said carriage is guided across a surface of said base;

a blade held by said carriage, said blade including a cutting edge; and a roller rotatably connected to said carriage in a position forward of said cutting edge of said blade, said roller pressing down on a portion of the patient's eye prior to said portion encountering said cutting edge of said blade.

11. The microkeratome according to claim 10, wherein said roller has an axis of rotation which is perpendicular to a direction of travel of said carriage across said base.

12. The microkeratome according to claim 10, wherein said roller has an axis of rotation which is parallel to said cutting edge.

13. The microkeratome according to claim 10, wherein said roller is one of cylindrical-shaped, barrel-shaped, and diabolo-shaped.

14. The microkeratome according to claim 10, wherein said roller is cylindrical-shaped and possesses a projection formed on its outer surface, which projection has a shape corresponding to a lens of an eye.

15. The microkeratome according to claim 10, wherein said roller is cylindrical-shaped and possesses a recess formed in its outer surface, which recess has a shape corresponding to a lens of an eye.

16. The microkeratome according to claim 10, further comprising:

an index mark fixed on a portion of said roller; and a reference mark fixed on a portion of said carriage, such that said index mark can be aligned with said reference mark to set said roller at a predetermined position.

17. The microkeratome according to claim 10, wherein a peripheral surface of said roller is provided with microrelief to enhance rolling without slip on the surface of the cornea.

18. The microkeratome according to claim 10, further comprising:

a plate attached to said carriage and position forward of said roller to engage of portion of the cornea prior to its engagement by said roller.

19. The microkeratome according to claim 18, wherein said plate is transparent and includes graduations forming a template for inspecting the cornea.

20. The microkeratome according to claim 10, wherein said base has a groove for facing towards the eye of the patient, said groove being partitioned into first and second portions by an intermediate wall, and wherein said intermediate wall includes at least one notch providing communication between said first and second portions of said groove.

21. The microkeratome according to claim 10, wherein said blade is driven to oscillate in said support.

* * * * *